United States Patent [19]
Camaggi et al.

[11] Patent Number: 5,334,609
[45] Date of Patent: Aug. 2, 1994

[54] THIAZOLE DERIVATIVES OF ALKOXYACRYLATES WITH A FUNGICIDAL ACTIVITY

[75] Inventors: Giovanni Camaggi, Novara; Lucio Filippini, San Donato Milanese; Marilena Gusmeroli, Monza; Raul Riva, Novara; Carlo Garavaglia, Cuggiono; Luigi Mirenna, Milan, all of Italy

[73] Assignee: Ministero dell'Universita' e della Ricerca Scientifica e Technologica, Rome, Italy

[21] Appl. No.: 14,219

[22] Filed: Feb. 5, 1993

[30] Foreign Application Priority Data

Feb. 6, 1992 [IT] Italy ............... MI92 A/000225

[51] Int. Cl.$^5$ .................. A01N 43/50; A01N 43/36; C07D 235/04
[52] U.S. Cl. .................. 514/393; 514/413; 548/303.1; 548/453
[58] Field of Search ............ 548/303.1, 453; 514/393, 413

[56] References Cited

PUBLICATIONS

J. C. Brindley et al., J. Chem. Soc., Perkin Trans. I, (1986) pp. 1255–1259.
G. D. Meakins et al., J. Chem. Soc., Perkin Trans. I, (1989) pp. 643–648.
European Journal of Medicinal Chemistry Chimica Therapeutica, vol. 25, No. 9, 1990—pp. 731–736.

Primary Examiner—Mary C. Lee
Assistant Examiner—Joseph K. McKane
Attorney, Agent, or Firm—Rogers & Wells

[57] ABSTRACT

Compounds based on derivatives of pyrrole[2,1-b]- and imidazo[2,1-b-]thiazoles, with a fungicidal activity, having the general formula (I):

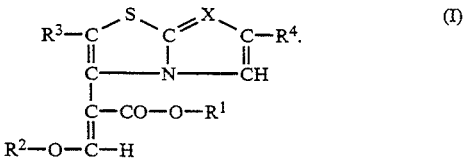

10 Claims, No Drawings

THIAZOLE DERIVATIVES OF ALKOXYACRYLATES WITH A FUNGICIDAL ACTIVITY

The present invention relates to compounds based on derivatives of pyrrole]2,1-b]- and imidazo[2,1-b] thiazoles.

More specifically, the present invention relates to compounds based on derivatives of pyrrole[2,1-b]-and imidazo[2,1-b]thiazoles having a high fungicidal activity, a procedure for their preparation and their use in agriculture as fungicides.

The present invention consequently relates to compounds based on derivatives of pyrrole[2,1-b]- and imidazo[2,1-b]thiazoles having the general formula (I):

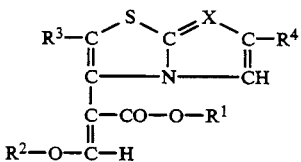

wherein:

X represents a nitrogen atom or the group

$R^1$, $R^2$ and $R^3$, the same or different, represent a hydrogen atom, a $C_1$-$C_6$ alkyl or haloalkyl group, either linear or branched;

$R^4$ represents a hydrogen atom, a $C_1$-$C_6$ alkyl group, linear or branched, a phenyl group, optionally substituted with:

halogens, such as chlorine, bromine, iodine;
$C_1$-$C_4$ alkyl radicals;
$C_1$-$C_4$ alkoxy or haloalkoxy radicals;
phenyl or phenoxyl radicals.

The structure having general formula (I) may have at least one E/Z isomerism.

The products having general formula (I) are antifungal agents for agricultural purposes.

Examples of $R^1$, $R^2$ and $R^3$ radicals are: methyl, ethyl, trifluoromethyl, 1,1,2,2-tetrafluoroethyl, etc.

Examples of $R^4$ radicals are: methyl, isopropyl, terbutyl, trifluoromethyl, 4-chlorobenzyl, 2,4-dichlorobenzyl, phenoxymethyl, 4-chlorophenoxymethyl, 2,4-dichlorophenoxymethyl, phenyl, 4-fluorophenyl, 2,4-difluorophenyl, 4-bromophenyl, 2,4-dibromophenyl, 2,4-dimethoxyphenyl, 4-(1,1,2,2-tetrafluoroethoxy)phenyl, 2,4-dimethylphenyl, 4-isopropylphenyl, 4-trifluoromethylphenyl, 3-trifluoromethylphenyl, 4-phenylphenyl, 4-phenoxyphenyl, 3-phenoxyphenyl, etc.

Compounds having general formula (I) not illustrated in the examples, but equally interesting for their fungicidal activity, are: (Z)-3-methoxy-2-[6-(methyl)imidazo[2,1-b]-thiazol-3-yl]methyl acrylate, (Z)-3-methoxy-2-[6-(trifluoromethyl)imidazo[2,1-b]-thiazol-3-yl]methyl acrylate, (Z)-3-methoxy-2-[6-(phenoxymethyl)imidazo[2,1-b]-thiazol-3-yl]methyl acrylate, (Z)-3-methoxy-2-[6-(phenyl) imidazo[2,1-b]-thiazol-3-yl]methyl acrylate, (Z)-3-methoxy-2-[6-(4-chlorophenoxymethyl)imidazo[2,1-b]-thiazol-3-yl]methyl acrylate, (Z)-3-methoxy-2-[6-(4-trifluoromethylphenyl) imidazo[2,1-b]-thiazol-3-yl]methyl acrylate, (Z)-3-methoxy-2-[6-(2,4-dichlorophenoxymethyl)imidazo[2,1-b]-thiazol-3-yl]methyl acrylate, (Z)-3-methoxy-2-[6-(2,4-dimethoxyhenyl)imidazo[2,1-b]-thiazol-3-yl]methyl acrylate, (Z)-3-methoxy-2-[6- (4-(1,1,2,2-tetrafluoroethoxy) phenyl)imidazo[2,1-b]-thiazol-3-yl]methyl acrylate, (Z)-3-methoxy-2-[6-(4-fluorophenyl) imidazo[2,1-b]-thiazol-3-yl]methyl acrylate, (Z)-3-methoxy-2-[6-(2,4-dimethylphenyl)imidazo[2,1-b]-thiazol-3-yl]methyl acrylate, (Z)-3-methoxy-2-[6-(2,4-difluorophenyl)imidazo[2,1-b]-thiazol-3-yl]methyl acrylate, (Z)-3-methoxy-2-[6-(4-isopropylphenyl) imidazo[2,1-b]-thiazol-3-yl]methyl acrylate, (Z)-3-methoxy-2-[6- (4-bromophenyl)imidazo[2,1-b]-thiazol-3-yl]methyl acrylate, (Z)-3-methoxy-2-[6-(4-phenylphenyl)imidazo[2,1-b]-thiazol-3-yl]methyl acrylate, (Z)-3-methoxy-2-[6-(2,4-dibromophenyl)imidazo[2,1-b]-thiazol-3-yl]methyl acrylate; or (Z)-3-methoxy-2-[6-(methyl) pyrrole[2,1-b]-thiazol-3-yl]methyl acrylate, (Z)-3-methoxy-2-[6-(trifluoromethyl) pyrrole[2, 1-b]-thiazole-3-yl]methyl acrylate, (Z)-3-methoxy-2-[6-(phenoxymethyl)pyrrole[2,1-b]-thiazol-3-yl]methyl acrylate, (Z)-3-methoxy- 2-[6-(phenyl)pyrrole[2,1-b]-thiazol-3-yl]methyl acrylate, (Z)-3-methoxy-2-[6- (4-chlorophenoxymethyl) pyrrole[2,1-b]-thiazol-3-yl]methyl acrylate, (Z)-3-methoxy-2-[6- (4-trifluoromethylphenyl) pyrrole[2,1-b]-thiazol-3-yl]methyl acrylate, (Z)-3-methoxy-2-[6- (2,4-dichlorophenoxymethyl)pyrrole[2,1-b]-thiazol-B-yl]methyl acrylate, (Z)-3-methoxy-2-[6- (2,4-dimethoxyphenyl)pyrrole[2, 1-b]-thiazol -3-yl]methyl acrylate, (Z)-3-methoxy-2-[6-(4-(1,1,2,2-tetrafluoroethoxy)phenyl)pyrrole[2,1-b]-thiazol-3-yl]methyl acrylate, (Z)-3-methoxy-2-[6-(4-fluorophenyl) pyrrole[2,1-b]-thiazol-3-yl]methyl acrylate, (Z)-3-methoxy-2-[6-(2, 4-dimethylphenyl)pyrrole[2, 1-b]-thiazol-3-yl]methyl acrylate, (Z)-3-methoxy-2-[6-(2,4-difluorophenyl)pyrrole[2, 1-b]-thiazol -3-yl]methyl acrylate, (Z)-3-methoxy-2-[6- (4-isopropylphenyl) pyrrole[2,1-b]-thiazol-3-yl]methyl acrylate, (Z)-3-methoxy-2-[6- (4-bromophenyl)pyrrole[2,1-b]-thiazol-3-yl]methyl acrylate, (Z)-3-methoxy-2-[6- (4-phenylphenyl)pyrrole[2,1-b]-thiazol-3-yl]methyl acrylate, (Z)-3-methoxy-2-[6- (2,4-dibromophenyl) pyrrole[2,1-b]-thiazol-3-yl]methyl acrylate, etc.

The compounds of the present invention can be obtained by the reaction of a thiazole derivative having general formula (II):

$$R^3-C\overset{S}{\underset{\underset{CH_2-CO-O-R^1}{|}}{\overset{|}{C}}}\underset{N}{\overset{X}{\diagdown}}C-R^4 \quad (II)$$

wherein $R^1$, $R^2$, $R^3$ and X have the meaning defined above, with an alkyl formiate having the general formula (III):

$$H-\overset{O}{\overset{\|}{C}}-O-R^5 \quad (III)$$

wherein $R^5$ represents a $C_{1-3}$ alkyl group, in an ether solvent, such as ethyl ether, and in the presence of a base, such as for example sodium hydride or potassium ter-butylate, at a temperature ranging from $-10°$ C. to $30°$ C., thus obtaining the salt having general formula (IV):

$$\begin{array}{c} R^3-C\overset{S}{\diagdown}C\overset{X}{\diagdown}C-R^4 \\ \|\qquad\qquad\| \\ C\!-\!-\!-\!N\!-\!-\!-\!CH \\ | \\ C-CO-O-R^1 \\ \| \\ H-O-CH \end{array} \qquad (IV)$$

wherefrom, by reaction with an alkylating agent $R^2$-Y, wherein $R^2$ has the meaning described above and Y represents a halogen atom, such as chlorine, bromine and iodine, or an activated ester, such as p-toluensulphonate, at a temperature of between $-10°$ C. and $30°$ C., the desired compound having general formula (I) is obtained.

The compounds having general formula (II) can be obtained with different procedures described in literature such as for example in: "Journal Chemical Society", Perkin Trans I, pages 1255–1259 (1986); "Journal Chemical Society", Perkin Trans I, pages 643–648, (1989).

The compounds having general formula (I) have a particularly high fungicidal activity against phytopathogen fungi which attack cultivations of vines, cereals, Cocurbitacee and fruit trees.

They have both a preventive and curative activity when applied to useful plants or their parts, such as leaves, and are particularly effective in preventing diseases caused by obligate pathogenic fungi, such as, for example, those belonging to the species Erysiphe and Helminthosporium.

Plant diseases which can be fought with the compounds of the present invention are, for example, the following:

Helminthosporium of cereals;
*Plasmopara viticola* of vines;
Phytium of horticultural products;
*Sphaerotheca fuliqinea* of cocurbitacee (e.g. cucumber);
Septoria of cereals;
*Erysiphe graminis* of cereals;
Rhynchosporium of cereals;
*Podosphaera leucotricha* of apple-trees;
Uncinula necator of vines;
*Venturia inequalis* of apple-trees;
*Piricularia oryzae* of rice;
Botrytis cinera;
Fusarium of cereals; etc.

The compounds having general formula (I), as well as carrying out both a curative and preventive fungicidal action as described above, also have a limited or non-existing phytotoxicity.

For practical uses in agriculture it is often useful to have fungicidal compositions containing one or more compounds of general formula (I), possibly also in an isomeric form, as an active substance.

These compositions can be applied on any part of the plant, for example on the leaves, stems, branches and roots, or on the seeds, before sowing, or also on the soil where the plant grows.

Compositions can be used in the form of dry powders, wettable powders, emulsifiable concentrates, micro-emulsions, pastes, granules, solutions, suspensions, etc.: the choice of the type of composition depends on the specific use.

The compositions are prepared according to the known procedures, for example by diluting or dissolving the active substance with a solvent medium and/or solid diluent, possibly in the presence of surface-active agents.

Solid diluents, or supports, which can be used are: silica, kaolin, bentonire, talc, infusorial earth, dolomite, calcium carbonate, magnesia, chalk, clays, synthetic silicates, attapulgite, sepiolite.

Liquid diluents, as well as water naturally, which can be used are various types of solvents, for example aromatic solvents (xylols, or mixtures of alkylbenzols), chloro aromatics (chlorobenzols), paraffins (fractions of petroleum), alcohols (methanol, propanol, butanol, octanol), amines, amides (N,N'-dimethylformamide, N-methylpyrrolidone), ketones (acetone, cyclohexanone, acetophenone, isophorone, ethylamylketone), esters (isobutyl acetate).

Surface-active agents which can be used are salts of sodium, calcium or of triethanolamine of alkylsulphates, alkylsulphonates, alkylarylsulphonates, polyethoxylated alkylphenols, fat alcohols condensed with ethylene oxide, polyoxyethylated fatty acids, polyoxyethylated esters of sorbitol, ligninsulphonates.

The compositions may also contain special additives for specific purposes, such as for example adhering agents such as arabic rubber, polyvinyl alcohol, polyvinylpyrrolidone.

If desired it is also possible to add other compatible active substances to the compositions of the present invention, such as fungicides, phytoregulators, antibiotics, weed-killers, insecticides, fertilizers.

The concentration of active substance in the above compositions can vary within a wide range, depending on the active compound, cultivation, pathogen, environmental conditions and type of formulation used.

In general the concentration of active substance varies from 0.1 to 95%, preferably from 0.5 to 90%.

The following examples provide an illustration of the present invention but do not limit it in any way.

EXAMPLE 1

Preparation of (Z)-3-methoxy-2-[6-(4-chlorophenyl)imidazo[2,1-b]-thiazol-3-yl]methyl acrylate (Compound No. 1)

1.62 g of sodium methylate are dispersed in 10 cm$^3$ of ethyl ether, in a nitrogen atmosphere.

6.40 g of[6-(4-chlorophenyl)imidazo[2,1-b]-thiazol-3-yl]methyl acetate in 10 cm$^3$ *of methyl formiate and* 10 cm$^3$ of ethyl ether are then added to the solution dropwise, over a period of 30 minutes.

The mixture thus obtained is kept for 4 hours at room temperature.

It is cooled to 5° C. and 12.4 cm$^3$ of CH$_3$I are added.

The solution is concentrated at reduced pressure and the crude product obtained is purified on silica gel, eluting with hexane:ethyl acetate in a ratio of 7:3.

3.6 g of compound No.1 are obtained, with a yield of 49.5%, the structure of which is shown in table 1.

Table 2 shows the NMR spectroscopic data of compound No.1.

EXAMPLES 2–4

Using the same procedure as example 1, compounds 2–4 were prepared the structure of which is shown in table 1.

The respective NMR data are shown in table 2.

EXAMPLE 5

Determination of the preventive fungicidal activity against *Helminthosporium teres*.

Leaves of barley cultivar Arna, grown in vases in a conditioned environment, are treated by spraying both sides of the leaves with compounds No.1 and 2 in a 20% by volume hydroacetonic solution in acetone (the concentration of the fungicide is 30 ppm).

After remaining two days in a conditioned environment at 20° C. and 70% relative humidity, the plants were sprayed on both sides of the leaves with an aqueous suspension of conidia of *Helminthosporium teres* (250000 conidia per cm3).

After remaining 24 hours in a humidity-saturated environment, at 21° C., the plants were kept in a conditioned environment for the incubation of the fungus.

At the end of this period (12 days), complete control of the disease was obtained.

TABLE 1

| Compound | (*) | X | $R^1$ | $R^2$ | $R^3$ | $R^4$ |
|---|---|---|---|---|---|---|
| 1 | E | N | $CH_3$ | $CH_3$ | H | 4-chlorophenyl |
| 2 | E | N | $CH_1$—$CH_3$ | $CH_3$ | H | 4-chlorophenyl |
| 3 | E | N | $CH_3$ | $CH_3$ | H | t-butyl |
| 4 | E | N | $CH_3$ | $CH_3$ | H | 2,4-dichlorophenyl |

(*) = isomerism of the 3-alkoxyacrylic group

TABLE 2

| Compound | NMR 200 MHz spectroscopy data (DMSO-$D^6$) |
|---|---|
| 1 | 3.7(3H)s, 4.0(3H)s, 7.1(1H)s, 7.4(2H)d, 7.9(2H)d, 8.0(1H)s, 8.1(1H)s. |
| 2 | 1.2(3H)t, 4.0(3H)s, 4.2(2H)q, 7.1(1H)s, 7.4(2H)d, 7.9(2H)d, 8.0(1H)s, 8.1(1H)s, |
| 3 | 1.3(9H)s, 3.7(3H)s, 3.9(3H)s, 6.6(1H)s, 6.8(1H)s, 7.7(1H)s. |
| 4 | 3.7(3H)s, 3.9(3H)s, 6.7(1H)s, 7.3(2H)m, 7.7(1H)s, 7.8(1H)s, 8.0(1H)m. |

We claim:

1. Pyrrole[2,1-*b*]- and imidazo[2,1-*b*]thiazole compounds having the general formula (I):

$$R^3-C\overset{S}{\underset{\underset{R^2-O-C-H}{\overset{|}{C}-CO-O-R^1}}{\diagup}}C\overset{X}{\underset{N}{\diagdown}}\overset{}{\underset{CH}{\diagup}}C-R^4 \qquad (I)$$

wherein:

X represents a nitrogen atom or the group $$=\underset{|}{C}-H;$$

$R^1$, $R^2$ and $R^3$, the same or different, represent a hydrogen atom, a $C_1$-$C_6$ alkyl or haloalkyl group, either linear or branched;

$R^4$ represents a hydrogen atom, a $C_1$-$C_6$ alkyl group, linear or branched, a phenyl group, optionally substituted with:
halogens;
$C_1$-$C_4$ alkyl radicals;
$C_1$-$C_4$ alkoxy or haloalkoxy radicals;
phenyl or phenoxyl radicals.

2. Antifungal agents for agricultural purposes comprised of pyrrole[2,1-b]- and imidazo[2,1-b]thiazole compounds having general formula (I):

$$R^3-C\overset{S}{\underset{\underset{R^2-O-C-H}{\overset{|}{C}-CO-O-R^1}}{\diagup}}C\overset{X}{\underset{N}{\diagdown}}\overset{}{\underset{CH}{\diagup}}C-R^4 \qquad (I)$$

wherein:

X represents a nitrogen atom or the group $$=\underset{|}{C}-H;$$

$R^1$, $R^2$ and $R^3$, the same or different represent a hydrogen atom, a $C_1$-$C_6$ alkyl or haloalkyl group, either linear or branched;

$R^4$ represents a hydrogen atom, a $C_1$-$C_6$ alkyl group, linear or branched, a phenyl group, optionally substituted with:
halogens selected from the group consisting of bromine and iodine;
$C_1$-$C_4$ alkyl radicals;
$C_1$-$C_4$ alkoxy or haloalkoxy radials;
phenyl or phenoxyl radicals.

3. Antifungal agents for agricultural purposes according to claim 2, wherein $R^1$, $R^2$ and $R^3$ are: methyl, ethyl, trifluoromethyl, 1,1,2,2-tetrafluoroethyl.

4. Antifungal agents for agricultural purposes according to claim 2, wherein $R^4$ is: methyl, isopropyl, ter-butyl, trifluoromethyl, 4-chlorobenzyl, 2,4-dichlorobenzyl, phenoxymethyl, 4-chlorophenoxymethyl, 2,4-dichlorophenoxymethyl, phenyl, 4-fluorophenyl, 2,4-difluorophenyl, 4-bromophenyl, 2,4-dibromophenyl, 2,4-dimethoxyphenyl, 4-(1,1,2,2-tetrafluoroethoxy)phenyl, 2,4-dimethylphenyl, 4-isopropylphenyl, 4-trifluoromethylphenyl, 3-trifluoromethylphenyl, 4-phenylphenyl, 4-phenoxyphenyl, 3-phenoxyphenyl.

5. Antifungal agent for agricultural purposes according to claim 2, composed of (Z)-3-methoxy-2-[6-(4-chlorophenyl)imidazo[2,1-b]-thiazol-3-yl]methyl acrylate.

6. Antifungal agent for agricultural purposes according to claim 2, composed of (Z)-3-methoxy-2-[6-(4-chlorophenyl)imidazo[2,1-b]-thiazol-3-yl]ethyl acrylate.

7. Antifungal agent for agricultural purposes according to claim 2, composed of (Z)-3-methoxy-2-[(6-ter-butyl)imidazo[2,1-b]-thiazol-3-yl]methyl acrylate.

8. Antifungal agent for agricultural purposes according to claim 2, composed of (Z)-3-methoxy-2-[6-(2,4-dichlorophenyl)imidazo[2,1-b]-thiazol-3-yl]methyl acrylate.

9. Fungicidal compositions containing one or more of the antifungal agents according to claim 2, along or in the presence of solid supports, liquid diluents, surface-active agents or other active principles.

10. Method for fighting fungal infections consisting in applying the fungicidal compositions according to claim 9 on plants, leaves, stems, branches and roots, or on the seeds before sowing, or on the soil where the plant grows.

* * * * *

UNITED STATES PATENT AND TRADEMARK OFFICE
CERTIFICATE OF CORRECTION

PATENT NO. : 5,334,609

DATED : August 2, 1994

INVENTOR(S) : Giovanni Camaggi; Lucio Filippini; Marilena Gusmeroli; Raul Riva; Carlo Garavaglia; and Luigi Mirenna It is certified that error appears in the above-indentified patent and that said Letters Patent is hereby corrected as shown below:

On the cover page of the patent, under the heading "[73] Assignee", it should read as --Ministero Dell'Universita' E Della Ricerca Scientifica E Tecnologica--;

In Claim 2, in line 28 (column 6), the word "radials" should read as --radicals--;

In Claim 9, in line 2 (column 6), the word "along" should read as --alone--.

Signed and Sealed this

Twentieth Day of December, 1994

Attest:

BRUCE LEHMAN

Attesting Officer

Commissioner of Patents and Trademarks